United States Patent [19]

Allas et al.

[11] Patent Number: 5,672,646
[45] Date of Patent: Sep. 30, 1997

[54] STABILIZING COMPOSITION FOR CHLORINE-CONTAINING POLYMER COMPRISING β-DIKETONES

[75] Inventors: Michel Allas; Serge Chassaing, both of Melle; Michel Gay, Villeurbanne; Gilles Mur, Saint Maur des Fosses, all of France

[73] Assignee: Rhone-Poulenc Chimie, Courbevoie, France

[21] Appl. No.: 642,973

[22] Filed: May 6, 1996

Related U.S. Application Data

[62] Division of Ser. No. 354,536, Dec. 13, 1994, abandoned.

[30] Foreign Application Priority Data

Dec. 15, 1993 [FR] France ................... 93 15064

[51] Int. Cl.⁶ .................. C08K 5/07; C08K 3/10; C08K 5/09
[52] U.S. Cl. .................. 524/357; 524/114; 524/127; 524/400; 524/423; 524/425; 524/567
[58] Field of Search .................. 524/357, 400, 524/423, 425, 567

[56] References Cited

U.S. PATENT DOCUMENTS

| | | | |
|---|---|---|---|
| 4,102,839 | 7/1978 | Crochemore et al. | 524/357 |
| 4,427,816 | 1/1984 | Aoki et al. | 524/357 |
| 5,070,128 | 12/1991 | Gay | 524/400 |
| 5,071,898 | 12/1991 | Wirth et al. | 524/357 |
| 5,252,645 | 10/1993 | Nosu et al. | 524/357 |

FOREIGN PATENT DOCUMENTS 0046161  2/1982  European Pat. Off. .

*Primary Examiner*—Tae Yoon
*Attorney, Agent, or Firm*—Andrew M. Solomon

[57] ABSTRACT

The present invention relates to a stabilizing composition for a chlorine-containing polymer (PVC), characterized in that it comprises the unpurified crude product resulting from the reaction of an ester with a ketone in the presence of an alkaline agent, this crude product comprising at least 10 % by weight of β-diketone and being in the form of a powder.

15 Claims, No Drawings

STABILIZING COMPOSITION FOR CHLORINE-CONTAINING POLYMER COMPRISING β-DIKETONES

This application is a division of application Ser. No. 08/354,536 filed Dec. 13, 1994 which application is now abandoned.

The present invention relates to a stabilizing composition for chlorine-containing polymer, comprising β-diketones and to the shaped objects obtained from the said compositions.

β-Diketones are a class of compounds which benefit from very diverse commercial applications, in particular in the extraction of metals and in the stabilization of chlorine-containing polymers.

Today β-diketones are the best organic stabilizers which are readily available for chlorine-containing polymers such as PVC. This is why these compounds have become increasingly important commercially.

The cost of manufacture of β-diketones can, however, delay their development. In fact, it is economically quite unthinkable to employ stabilizers which are too costly in the industry of chlorine-containing polymers (PVC).

After having carried out long and costly research, the Applicant Company has found, completely unexpectedly, that a stabilizing composition for chlorine-containing polymer (PVC), comprising the unpurified crude product resulting from the condensation reaction of an ester with a ketone in the presence of an alkaline agent, this crude product comprising between 10% and 95%, preferably between 20 and 85%, by weight of β-diketone and being in the form of a powder, has, in identical weight, a stabilizing action which is at least equal to that which a stabilizing composition comprising recrystallized, purified β-diketone would have had, everything else being otherwise equal.

This condensation reaction of an ester with a ketone can be written:

$$R_1COCHR_2H + R_3CO\text{---}OR_4 + ACat \rightarrow R_1COCHR_2COR_3 + R_4OH$$

where:
- A Cat is chosen from an amide of a cation or a hydride of a cation,
- each of $R_1$ and $R_3$, which may be similar or different, denotes a hydrocarbon radical which has advantageously from 1 to 30 carbon atoms, preferably from 1 to 18 carbon atoms,
- $R_2$ is hydrogen or a hydrocarbon radical, generally alkyl, advantageously containing not more than 4 carbon atoms,
- it being possible for $R_1$ and $R_2$ to be joined so that the β-diketone forms a ring,
- $R_4$ denotes a hydrocarbon radical.

With regard to the value of radicals $R_1$, $R_2$ and $R_3$, a wide spectrum of radicals may be employed, thus:
- $R_1$ and $R_2$, which may be identical or different, denoting:
  - a linear or branched aralkyl or alkenyl radical containing up to 24 carbon atoms,
  - an aralkyl radical containing from 7 to 10 carbon atoms,
  - an aryl or cycloaliphatic radical containing fewer than 14 carbon atoms, it being optionally possible for the cycloaliphatic radicals to contain carbon-carbon double bonds.

These radicals may be unsubstituted or substituted, for example by halogen atoms or, in the case of aryl or cycloaliphatic radicals, by methyl or ethyl radicals.

The radicals listed above may also be modified by the presence, in the aliphatic chain, of one or more of the groups of formula:

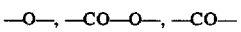

$R_1$ and $R_3$ may also denote, together, a divalent single radical containing from 2 to 5 carbon atoms and which may contain an oxygen or nitrogen heteroatom, $R_2$ may be:
- a hydrogen atom (preferred case)
- a substituted or unsubstituted alkyl radical containing from 1 to 4 carbon atoms and which may be interrupted by —O—, —CO—O and/or —CO— groups,
- $R_4$ denoting an alkyl radical containing from 1 to 4 carbon atoms, preferably methyl.

The cation Cat is generally an alkali metal, preferably sodium.

The condensation reaction described above is well known to a person skilled in the art. More particularly it is described especially in the following publications:

R. Hauser et al., "The acylation of ketones to form diketones", Organic Reactions, Vol. VII, Chapter 3, p. 59–196, John Wiley Publ. New York 1954

Wiedman et al., C. R. 238 (1954) p. 699

Morgan et al., Ber. 58 (1925) p. 333

Livingstone et al., Am. Soc. 46 (1924) p. 881–888

Robert Levine et al., Am. Soc. 67 (1945) p. 1510–1517, which are incorporated as references in the present description.

According to a preferred embodiment the choice of the starting reactants is based on the availability of these products and on the activity of the reaction products obtained; an ester is thus employed as preferred starting material.

In the case of the ester, methyl stearate especially of technical grade may then contain other fatty acid esters as impurity, in particular methyl palmitate, in the case of acetone, acetophenone, and in the case of the alkaline agent, sodium amide.

It is recommended to employ 2 moles of amide per mole of ester or of ketone introduced and to employ a slight molar excess (between 5 and 30%) of ketone relative to the ester.

Because of the presence of sodium amide it is preferable to perform the reaction under inert atmosphere, preferably under nitrogen flushing.

The reaction is performed at a temperature situated preferably between 30° and 70° C.

If the reaction is performed at Ambient temperature (20° C.), the kinetics are too slow. Furthermore, if the temperature is too high, for example 60° C. and more, such a temperature promotes, on the one hand, the autocondensation of ketones in general and of acetophenone in particular and, on the other hand, the formation of amides.

The solvents which can be employed are inert solvents of the ether type, especially isopropyl ether, aliphatic hydrocarbons (for example cyclohexane) or else aromatic hydrocarbons (toluene).

Although it is technically possible to conduct the reaction at a pressure higher than atmospheric pressure, it is preferred, for economic reasons, to work at atmospheric pressure or else at reduced pressure, so as to lower the temperatures indicated above and to bring them into a range of between 35° and 55° C. Pressures lower than $10^4$ Pa are rarely employed.

At the end of reaction the mixture must be acidified. To do this, the reaction solution is poured into an aqueous solution of an acid, the preferred ones being acetic acid, hydrochloric acid and sulphuric acid. The pH of the aqueous layer is adjusted to a value which is preferably between 1 and 3.

The following 3 operating methods may be envisaged in particular for introducing the reactants:

a) the enolate anion of acetophenone is formed beforehand by pouring acetophenone into the amide/solvent mixture, and the ester is then added, b) the solvent, the amide and all the ester are charged and acetophenone is then run in slowly, c) acetophenone and the ester are run in simultaneously into the amide/solvent mixture.

It is recommended to employ route b) and then to acidify the reaction mixture in a molar excess (1.2 to 2 times molar) of sulphuric acid diluted to 5–20% in water so that the pH is approximately 1.5.

After at least one washing with water the solvent is removed by any suitable means, for example by evaporation, and a crude product is obtained which is solid at ambient temperature, generally comprising between 40% and 90% by weight of β-diketone.

According to the invention it has been discovered that this crude product, once ground and reduced to the state of powder, can be employed directly as additive in a stabilizing composition for chlorine-containing polymer.

This powder has a particle size which is generally smaller than 500 μm, preferably smaller than 200 μm.

According to a particularly advantageous alternative form of the invention this crude product is ground in accordance with a particle size which is included in the range of the particle sizes of the additives of which the stabilizing composition consists. This particle size may be advantageously similar to the smallest particle size of the various additives. One of these additives may be, for example, an aluminium and/or magnesium carbonate and/or sulphate, for example of the hydrotalcite type and may then have a particle size smaller than 100 μm, generally between 20 and 100 μm, or else may be a calcium and/or barium stearate and may then also have a particle size which is much smaller than 100 μm, generally between 50 and 100 μm.

Any techniques known to a person skilled in the art may be employed to obtain the powders so as to finish with the desired particle size, and especially:

a) precipitation in a solvent, b) cryogenic grinding, c) countercurrent or concurrent spray-drying in a cold stream.

According to technique a) the solid crude product of the reaction is dissolved in an appropriate solvent such as, for example, ethanol or methanol, at ambient temperature, the solvent is distilled off at a reduced pressure of the order of $10^3$ Pa and nitrogen is then injected.

According to technique b), liquid nitrogen and the crude reaction product in the form of lumps from a few mm to a few cm, obtained by coarse grinding or else by the technique of "flaking" of the reaction solution, are introduced into a mill. The "flaking" makes it possible to remove the solvent from this reaction solution by passing the solution over a continuously cooled rotating drum. The product solidified at the surface of the drum is recovered by a scraper blade precisely in the form of "flakes".

Another inert liquid gas such as liquid $CO_2$ may be employed instead of liquid nitrogen.

According to technique c), the crude reaction product is sprayed in the molten state through a countercurrent or concurrent stream of a gas which is inert towards the product, such as air depleted in benzene. Microbeads of product are recovered, the particle size of which may be easily smaller than 100 μm and may go down to 10 μm.

According to a well-known technique the crude reaction product may be recrystallized from a suitable organic solvent, generally ethanol. The recrystallized product, separated by simple filtration from the mother liquors, is in the form of powder and is essentially made up of β-diketones. Purified β-diketones have to be employed for some applications. The use of β-diketones purified to more than 95% by weight in stabilizing compositions for graft polymer does not form part of the present invention.

In contrast, according to the invention it has been found that, after removal of the crystallization solvent by any suitable method (for example by evaporation or by the flaking technique mentioned above), the mother liquors produce a solid recrystallization residue which then generally comprises at least 10% and in most cases between 20 and 40% of β-diketones, and that this crystallization residue, also converted into powder form, has, in equal weight, a stabilizing action on the polymers which is substantially equal to that which the same weight of a stabilizing composition based on recrystallized purified β-diketone would have had.

These heavy solid recrystallization residues are employed in the same way as the crude reaction product and are converted into powder by the same methods.

An acceptable stabilization of the chlorine-containing polymers and more particularly of PVC in most cases requires the combined use of a number of stabilizers which act in a complementary and sometimes synergistic manner.

Thus, besides the crude reaction product and/or the heavy recrystallization residues in the form of powder, the stabilizing compositions according to the invention may contain an effective quantity of at least one additive chosen especially from:

a) an aluminum and/or magnesium sulphate and/or carbonate, especially of the hydrotalcite type. Such products are described, for example, in Patents U.S. Pat. Nos. 4,299,759, 4,427,816, EP-A-453,379 and EP-A-509,864, b) an organic alcohol or polyol in accordance with the teaching of FR-A-2,356,674 and FR-A-2,356,695, c) a lead compound like those described especially in the Encyclopedia of PVC by Leonard I. Nass (1976) pages 299–303, d) a salt of a metal chosen from calcium, barium, magnesium and strontium (EP-A-391,311), e) an organic zinc compound (EP-A-391,811), f) an organic phosphate, especially trialkyl or alkyl phenyl or triphenyl phosphates (EP-A-391,811), g) an organotin compound (EP-A-509,864), h) a polyorganosiloxane oil (EP-A-509,864), i) epoxides, which are generally complex compounds, usually epoxidized polyglycerides, epoxidized linseed oil and epoxidized fish oils, j) usual adjuvants such as phenolic antioxidants, and anti-UV agents such as benzophenones, benzotriazoles or sterically hindered amines (usually known as SHAs).

In general, any type of PVC is suitable, whatever its method of preparation: polymerization in bulk, in suspension, in emulsion or of any other type and whatever its intrinsic viscosity.

Vinyl chloride homopolymers can also be modified chemically, for example by chlorination. Many vinyl chloride copolymers can also be stabilized against the effects of heat, that is to say yellowing and degradation. They are, in particular, the copolymers obtained by copolymerization of vinyl chloride with other monomers containing a polymerizable ethylenic bond, such as, for example, vinyl acetate or vinylidene chloride, maleic or fumaric acids or their esters, olefins such as ethylene, propylene and hexene, acrylic or methacrylic esters, styrene, and vinyl ethers such as vinyl dodecyl ether.

These copolymers usually contain at least 50% by weight of vinyl chloride units and preferably at least 80% by weight of vinyl chloride units.

The compositions according to the invention may also contain mixtures based on chlorine-containing polymer, containing minor quantities of other polymers, such as halogenated polyolefins or acrylonitrile-butadiene-styrene copolymers.

PVC by itself or mixed with other polymers is the chlorine-containing polymer most widely employed in the compositions of the invention.

The compositions of the invention may be rigid formulations, that is to say without plasticizer, or semirigid ones, that is to say with low plasticizer contents, such as for applications in building, the manufacture of various sections or electrical cable production, or compositions containing only food-contact grade additives, for bottle manufacture.

In most cases these formulations contain an impact improver such as, for example a methacrylate/butadiene/styrene copolymer.

They may also be plasticized formulations such as for the manufacture of films for agricultural use.

The plasticizers employed are known compounds such as, for example, alkyl phthalates. Di(2-ethylhexyl) phthalate (usually called dioctyl phthalate) is employed in most cases.

When the compositions contain a plasticizer, the content of the latter is generally from 5% to 120% by weight relative to the weight of chlorine-containing polymer.

The presence of basic aluminium and magnesium carbonate in the compositions of the invention introduces a certain number of advantages.

Thus, in compositions containing lead compounds, basic aluminium magnesium carbonate of formula (i) makes it possible to reduce the quantity of the lead compound and optionally of the cadmium compound when it is present, without decreasing the thermal stability of the polymer, which is a positive factor because compounds which exhibit a certain toxicity are partially replaced with a potentially alimentary compound.

Incorporation of the various stabilizers or adjuvants is, as usual, generally performed on the chlorine-containing polymer in powder form, premixing of the various solid adjuvants being in most cases performed beforehand.

A mixture of two or more of the compounds of which the compositions according to the invention consist can, of course, be prepared before they are incorporated into the chlorine-containing polymer.

Any of the usual methods for incorporating various stabilizers or adjuvants into the polymer may be employed. For example, homogenizing of the polymeric composition may be carried out in a mixer or on a roll mill, at a temperature such that the composition becomes fluid, normally between 150° C. and 200° C. in the case of PVC, and for a sufficient period, of the order of a few minutes to some tens of minutes.

The chlorine-containing polymer compositions, and more particularly PVC, may be processed by any of the techniques usually employed, such as, for example, extrusion, injection moulding, blow-extrusion, calendering or rotational moulding.

The examples which follow illustrate the invention.

In what follows or what precedes, the parts and percentages are by weight, unless the contrary is expressly stated.

EXAMPLE 1

Preparation of the crude reaction product P1

The following is introduced into a 2,000 cm$^3$ reactor fitted with a condenser, good stirring and with the possibility of being connected either to vacuum or to a source of nitrogen:

toluene 260 ml and then, under nitrogen blanketing:

NaNH$_2$ 78 g

The temperature of the mixture is then raised to 40° C. and maintained at this temperature throughout the reaction and the finishing.

The whole apparatus is brought to a pressure of 6×10$^4$ Pa.

310 g of technical methyl stearate (containing 10% of methyl palmitate) are run in.

120 g of acetophenone are run in over 3 hours.

When the addition of acetophenone is finished, the reaction mixture is left stirred for 45 min (temperature of 40° C. and at a pressure of 6×10$^4$ Pa).

The toluene solution is then poured while warm into a solution of sulphuric acid diluted to 10% so that the pH of the aqueous layer is 1.5 after separation.

After two washings, the toluene solution is next evaporated by running the solution over a continuously cooled rotating drum to produce a crude product P1 in the form of "flakes", that is 420 g of a product which is solid at 20° C., analysing at 78% of β-diketones (82% yield). (GPC chromatographic analysis).

EXAMPLE 2

Preparation of the heavy residues L1.

The operating method of Example 1 is repeated exactly. The toluene-free crude reaction product obtained is dissolved in 1500 ml of ethanol.

The solution is filtered and drained on No. 2 glass sinter. Two washings with 500 ml portions of ethanol are then carried out in succession, followed by draining.

304 g of a pure product PP1 are obtained, analysing at 97% by weight of β-diketones.

Evaporation of the filtrate produces a product called heavy product L1, exhibiting a melting point situated between 40° and 45° C. and analysing at 28% by weight of β-diketones (GPC chromatographic analysis).

EXAMPLE 3

Preparation of a powder P1

3 parts of ethanol containing 7% of water are introduced at 20° C. into a stirred spherical reactor fitted with cooling means and with a three-bladed stirrer at the bottom of the vessel, and 1.0 part of P1 prepared according to the operating method of Example 1 and heated to 70° C. is run in over 1 hour. The temperature of the content of the reactor is maintained between 20° and 25° C. The reactor pressure is reduced to 2×10$^3$ Pa and the ethanol is distilled off, care being taken that the temperature in the bulk should not exceed 25° C. Nitrogen is then injected until traces of water have disappeared. A light-yellow powder P1 is obtained, the particle size of which is approximately 120 μm.

EXAMPLE 4

Preparation of a powder L1

The operating method of Example 3 is repeated exactly, except that 1 part of starting material P1 is replaced with 1 part of heavy material L1 obtained by the operating method of Example 2. A chestnut-brown powder is thus obtained, the particle size of which is approximately 130 μm.

EXAMPLE 5

Preparation of a powder P1

1 part/hour of product P1 of Example 1 and 0.3 part/hour of liquid nitrogen are introduced by means of a screw conveyor into a hammer mill equipped with a 1 mm grid. The ground product is recovered by pneumatic conveying towards a filter separation system and a white powder with a particle size of 50 μm as obtained.

A similar powder is obtained when P1 is replaced with L1 and the liquid nitrogen with liquid $CO_2$.

EXAMPLE 6

Preparation of a powder P1

1 part/hour of product P1 at 70° C., obtained according to Example 1 is fed, through a crown-ring of sprayers at the head of a prilling tower operating countercurrentwise. Approximately 10 parts/hour of air containing 8% (by volume) of oxygen, maintained at a temperature of between 15° and 20° C. are rotated countercurrentwise. 1 part/hour of P1 is recovered at the bottom of the tower, as spherical microbeads whose particle size is 40 μm. The oxygen-depleted air is recycled to the bottom of the tower after filtration and cooling to 15°/20° C.

A powder with a particle size of 100 μm is obtained. A similar result is obtained by replacing P1 with L1.

EXAMPLE 7

The starting point is a semirigid PVC powder composition which has the following composition:

| | |
|---|---|
| PVC powder prepared by suspension polymerization and marketed under the name SOLVIC 271 GB | 100 parts |
| DOP (dioctyl phthalate) | 25 parts |
| Calcium 2-ethyl hexanoate | 0.4 parts |
| Zinc octoate | 0.15 parts |
| Phosphite OS 150 ® (diphenyl isododecyl phosphite) | 1.0 part |
| PE 191 ® polar polyethylene wax marketed by Hoechst | 1.0 part |
| Irganox 1076 ® antioxidant marketed by Ciba-Geigy | 0.1 part |
| epoxidized soya oil | 3 parts |

From this composition, which is used as control, various samples are produced by adding 0.1, 0.2 and 0.3 parts, respectively, of powder L1 obtained according to Example 5, and of crystallized powder PP1 obtained in Example 2, per 100 parts of PVC resin, and homogenizing for 10 min with the aid of the CNTA B17 laboratory mixer.

Sheets of 1 mm thickness are prepared from the powders thus obtained by milling for 10 min at 180° C. on a 2-roll mill.

Test pieces 27.5 cm in length and 2 cm in width are cut from the sheets thus obtained. They are then arranged on a movable tray introduced into an oven at 190° C. and taken out at constant speed (0.45 cm/min) for 1 hour. This makes it possible to obtain the thermal degradation of the test piece as a function of the residence time (Metrastat test).

The thermal degradation is quantified by measuring the change in the yellowing index as a function of time with the aid of a Minolta CR200® chromometer on the (Y, x, y) scale. This makes it possible to obtain three significant parameters for comparison, namely:

- the initial colour (IC) which is the yellowing index at 2.5 min exposure (error ΔY=1.5),
- the colour stability (CS) (evaluated in minutes), which corresponds to the time at which the yellowing index changes by 2 points (error ΔT=2 min),
- long-term thermal stability (LTTS) (evaluated in minutes) or scorching time, which is the time when the degradation (blackening) of the test piece appears (error ΔT=4 min).

The results obtained are collated in Table 1 below.

From the inspection of Table 1 it appears that the use of L1 (heavy material from recrystallization) gives effects which are superior to PP1. This phenomenon is all the more marked in the case of colour stability.

In addition, like P1, L1 improves the long-term thermal stability.

TABLE 1

| Additive in parts per hundred parts of PVC resin | I.C. (%) | C.S. (min) | LTTS (min) |
|---|---|---|---|
| Control | 13.6 | 7.8 | 37 |
| 0.1 PP1 | 9.4 | 20 | 33 |
| 0.2 PP1 | 8.8 | 18.2 | 33 |
| 0.3 PP1 | 9.8 | 21 | 37 |
| 0.1 L1 | 10.2 | 20.6 | 36 |
| 0.2 L1 | 10.5 | 22 | 38 |
| 0.3 L1 | 14.7 | 24.8 | 44 |

EXAMPLE 8

The starting point is PVC composition (rigid formulation), which has the following composition:

| | |
|---|---|
| PVC powder prepared by suspension polymerization and marketed under the name S 110 P (Atochem): | 100 parts |
| Calcium stearate, stabilizer marketed by Atochem under reference Stavinor PSME | 0.7 parts |
| Zinc stearate, stabilizer marketed by Atochem under reference ZN 70 | 0.8 parts |
| Didecyl phenyl phosphite, stabilizer marketed by Ciba-Geigy under reference Irgastab CH 300 | 0.8 parts |
| Polyvinyl alcohol, stabilizer marketed by Erkol under reference Rhodiastab PVAL | 0.2 parts |
| Hydrotalcite (aluminium magnesium hydrogencarbonate), stabilizer marketed under reference Alcamizer 4 by Mitsui | 0.2 parts |
| Ground calcium carbonate, filler marketed under reference Omyalite 95T by Omya | 9.5 parts |
| Titanium oxide pigment marketed by Kronos under reference CL 2220 | 5 parts |
| Impact improver (acrylic polymer) marketed by Rohm and Haas under the name Paraloid KM 355 | 6.5 parts |
| Lubricants marketed by Henkel under the names: | |
| Loxiol G20 (ester of an aromatic diacid and of an aliphatic fatty alcohol) | 0.6 parts |
| Loxiol G30 (waxy ester) | 0.3 parts |
| Loxiol G21 (12-hydroxystearic acid) | 0.2 parts |

2 samples are prepared from this composition by adding:

0.25 parts of product P1 of Example 5

0.25 parts of product PP1 of Example 2

Each sample is homogenized for 10 minutes at 4500 rev/min with the aid of a CNTA B17 laboratory mixer.

From these powders, a dynamic thermal stability procedure is carried out in a Brabender® plastograph. This apparatus consists:

of an electrical motor system coupled to a continuous- or noncontinuous speed regulator (0 to 200 rev/min), of a thermostated bath with electronic proportional temperature control using silicone oil, of a mixer, fitted with a jacketed vessel permitting heating by circulating silicone oil and with 2 rotors fixed by a bayonnet locking system, of a chronometer.

Each test is introduced into this mixer at 150° C., in a quantity of 52 g, with the aid of a hopper and of a piston pushed by a 5 kg weight. Then, every 5 minutes, a sample is taken in order to obtain a pellet until the PVC mix blackens or is scorched.

The whiteness value (WV) according to the CIE (L, a, b) scale of ASTM standard E313 and the yellowing index (YI) which is measured according to the (Y, x, y) scale of ASTM standard D1925 are measured by colouring, with the aid of a Minolta CR200® chromometer on each pellet.

The thermal degradation of each formulation as a function of time is thus obtained.

The results obtained are collated in Table 2 below:

TABLE 2

| Time | Product P1 (Example 5) | Product PP1 (Example 2) |
|---|---|---|
| 5 min | YI = 7.3 | YI = 6.7 |
|  | WV = 63.5 | WV = 65.3 |
| 10 min | YI = 7.4 | YI = 8.3 |
|  | WV = 63.7 | WV = 62.2 |
| 15 min | YI = 8.3 | YI = 9.2 |
|  | WV = 61.3 | WV = 59.5 |
| 20 min | YI = 8.1 | YI = 9.1 |
|  | WV = 61.3 | WV = 60.0 |
| 25 min | YI = 8.4 | Scorching |
|  | WV = 61.1 |  |
| 30 min | Scorching |  |

Inspection of the table shows that the ground crude product P1 has a better thermal stability than the recrystallized product PP1; its yellowing index changes less rapidly with time and the whiteness is maintained at values which are higher than those obtained using the product PP1.

EXAMPLE 9

The starting point is a semirigid PVC powder composition which has the following composition:

| PVC powder prepared by suspension polymerization and marketed under the name SOLVIC 271 GB | 100 parts |
|---|---|
| DOP (dioctyl phthalate) | 25 parts |
| Calcium 2-ethylhexanoate | 0.4 parts |
| Zinc acetate | 0.15 parts |
| Phosphite OS 150 ® (diphenyl isodecyl phosphite) | 1.0 part |
| PE 191 ® polar polyethylene wax marketed by Hoechst | 1.0 part |
| Irganox 1076 ® antioxidant marketed by Ciba-Geigy | 0.1 part |
| epoxidized soya oil | 3 parts |

From this composition, which is used as control, various samples are produced by adding 0.1, 0.2 and 0.3 parts, respectively, of powder P1 and L1 obtained according to Example 5, and of crystallized powder PP1 obtained in Example 2, per 100 parts of PVC resin, and homogenizing for 10 min with the aid of the CNTA B17 laboratory mixer.

Sheets of 1 mm thickness are prepared from the powders thus obtained by milling for 10 min at 180° C. on a 2-roll mill.

Test pieces 27.5 cm in length and 2 cm in width are cut from the sheets thus obtained. They are then arranged on a movable tray introduced into an oven at 190° C. and taken out at constant speed (0.45 cm/min) for 1 hour. This makes it possible to obtain the thermal degradation of the test piece as a function of the residence time (Metrastat test).

The thermal degradation is quantified by measuring the change in the yellowing index as a function of time with the aid of a Minolta CR200® chromometer on the (Y, x, y) scale. This makes it possible to obtain three significant parameters for comparison, namely:

the initial colour (IC) which is the yellowing index at 2.5 min exposure (error ΔY=1.5), the colour stability (CS) (evaluated in minutes), which corresponds to the time at which the yellowing index changes by 2 points (error ΔT=2 min), long-term thermal stability (LTTS) (evaluated in minutes) or scorching time, which is the time when the degradation (blackening) of the test piece appears (error ΔT=4 min).

The results obtained are collated in Table 1 below.

From the inspection of Table 1, it appears that the stabilizing power of PP1 (recrystallized product) is, for the same weight, analogous to that of P1 (crude non-recrystallized reaction product), especially as regards the colour stability, the initial colour showing virtually the same change.

Moreover, the long-term thermal stability is improved, at an identical weight, by using P1 in place of PP1.

It is additionally noticed that the use of L1 (heavy material from recrystallization) gives effects analogous to PP1. This phenomenon is all the more marked in the case of colour stability.

In addition, like P1, L1 improves the long-term thermal stability.

TABLE 1

| Additive in parts per hundred parts of PVC resin | I.C. (%) | C.S. (min) | LTTS (min) |
|---|---|---|---|
| Control | 13.6 | 7.8 | 37 |
| 0.1 PP1 | 9.4 | 20 | 33 |
| 0.2 PP1 | 8.8 | 18.2 | 33 |
| 0.3 PP1 | 9.8 | 21 | 37 |
| 0.1 P1 | 10.0 | 12.9 | 39 |
| 0.2 P1 | 9.0 | 14.4 | 37.5 |
| 0.3 P1 | 8.9 | 11.5 | 38.5 |
| 0.1 L1 | 10.2 | 20.6 | 36 |
| 0.2 L1 | 10.5 | 22 | 38 |
| 0.3 L1 | 14.7 | 24.8 | 44 |

EXAMPLE 10

The starting point is a PVC composition (rigid formulation), which has the following composition:

| PVC powder prepared by suspension polymerization and marketed under the name S 110 P (Atochem): | 100 parts |
|---|---|
| Calcium stearate, stabilizer marketed by Atochem under reference Stavinor PSME | 0.7 part |
| Zinc stearate, stabilizer marketed by Atochem under reference ZN 70 | 0.8 part |
| Didecyl phenyl phosphite, stabilizer marketed by Ciba-Geigy under reference Irgastab CH 300 | 0.5 part |
| Polyvinyl alcohol, stabilizer marketed by RP Chimie under | 0.1 part |

-continued

| | |
|---|---|
| reference Rhodiastab PVAL | |
| Hydrotalcite (aluminium magnesium hydrogencarbonate), stabilizer marketed under reference Alcamizer 4 by Mitsui | 0.4 part |
| Ground calcium carbonate, filler marketed under reference Omyalite 95T by Omya | 9.5 parts |
| Titanium oxide pigment marketed by Kronos under reference CL 2220 | 5 parts |
| Impact improver (acrylic polymer) marketed by Rohm and Haas under the name Paraloid KM 355 | 6.5 parts |
| Lubricants marketed by Henkel under the names: | |
| Loxiol G60 (ester of an aromatic diacid and of an aliphatic fatty alcohol) | 0.4 part |
| Loxiol G21 (12-hydroxystearic acid) | 0.2 part |
| A processing aid marketed by Rohm and Haas under the name Paraloid Kron | 1 part |

Two samples are prepared from this composition by adding:

0.25 part of product P1 of Example 5

0.25 part of product P2

(P2=stearoylbenzoylmethane, which is outside the scope of the present invention).

Each sample is homogenized in a Papenmeler-type fast mixer at the rate of 1800 rev/min to a temperature of 115° C.

From these powders, an extrusion transformation is carried out in order to obtain panels.

The characteristics of the single-screw extruder are:

Manufacturer: Andouart

Conical screw: compression ratio=2.8 length/diameter ratio=20 diameter D=40 mm

The extrusion conditions are:

Rate of rotation of the screw=23 rev/min

Temperature profile:

| Zone 1 | 2 | 3 | Dies |
|---|---|---|---|
| 175° C. | 180° C. | 185° C. | 190° C. |

The panels thus extruded are subjected to UV radiation under two types of conditions:

1) Uvcon conditions:

Uvcon apparatus from Atlas Illumination spectrum:

UVA with a maximum at a=340 nm and filter <290 nm

Black body temperature=55° C. Atmosphere saturated with moisture

2) Xenotest conditions 1200 CPS Xenotest

Irradiance=80 W/m²

Chamber T (° C.)=30° C.

Cycle

=29 min sec >65% relative humidity

=1 min sec >99% relative humidity

3 Xenon lamps

Filter type: 3 suprax ⅓ filters

Black body

The resistance to UV light of each formulation as a function of time is thus obtained.

The results obtained are collated in Table 3 below:

TABLE 3

| | Uvcon conditions | | | Xenotest conditions | |
|---|---|---|---|---|---|
| | P1 | P2 | | P1 | P2 |
| Δb1 | 10.71 | 17.10 | Δb2 | 4.31 | 5.73 |

Δb1: difference in yellowing index between the exposure time of 600 h and the starting time.
Δb2: difference in yellowing index between the exposure time of 1000 h and the starting time.

From Table 3, it appears that P1, in accordance with the invention, has a yellowing index which changes less rapidly with time after exposure to UV light than P2, which is outside the scope of the invention.

We claim:

1. A chlorine containing polymer including a stabilizing composition wherein the stabilizing composition comprises:

(i) the crude product resulting from the condensation reaction of an ester with a ketone in the presence of a alkaline agent, wherein the said crude product comprises between 10 and 95 percent by weight of β-diketones and between 90 and 5% by weight of by-products from the condensation reaction, and wherein said crude product is in the form of a powder; and (ii) an effective quantity of a supplementary additive.

2. The composition according to claim 1 wherein said chlorine containing polymer comprises polyvinyl chloride.

3. The composition according to claim 1 wherein the crude product comprises between 20 and 85 percent by weight of β-diketones.

4. The composition according to claim 1 wherein the crude product is the solid residue obtained from the recrystallization residue of mother liquor of the said crude product.

5. The composition according to claim 4 wherein the solid recrystallization residue comprises between 20 and 40% by weight of beta-diketones.

6. The composition according to claim 1 wherein the condensation reaction is performed according to the reaction:

$$R_1COCHR_2H+R_3CO\text{---}OR_4+ACat\rightarrow R_1COCHR_2COR_3+R_4OH$$

with:

Acat is chosen from an amide of a cation or a hydride of a cation, each of $R_1$ and $R_3$, which may be similar or different, denotes a hydrocarbon radical which has from 1 to 30 carbon atoms, $R_2$ is hydrogen or a hydrocarbon radical, optionally $R_1$ and $R_2$ being joined so that the B-diketone forms a ring, $R_4$ denoted a hydrocarbon radical.

7. The composition according to claim 6 wherein each of $R_1$ and $R_3$ contains between from 1 to 18 carbon atoms and wherein $R_2$ is an alkyl group containing not more than 4 carbon atoms.

8. The composition according to claim 6 wherein $R_4$ is a methyl group.

9. The composition according to claim wherein $R_1$ and $R_3$, which may be identical or different, denote:

a linear or branched aralkyl or alkenyl radical containing up to 24 carbon atoms, an aralkyl radical containing 7 to 10 carbon atoms, an aryl or cycloaliphatic radical containing fewer than 14 carbon atoms, R4 denotes an alkyl radical containing from 1 to 4 carbon atoms.

10. The composition according to claim 9 wherein the ester is methyl stearate, ketone is acetophenone and the alkaline agent is sodium amide.

11. The composition according to claim 7 wherein the said powder has a particle size smaller than 500 micrometer.

12. The composition according to claim 11 wherein said powder has a particle size smaller than 200 μm.

13. The composition according to claim 1, wherein said supplementary additive is chosen from an aluminum and/or magnesium carbonate and/or sulfate, a hydrotalcite, calcium and/or barium stearate and in that the particle sizes of the supplementary additive and of the crude product are similar and smaller than 100 micrometer.

14. The composition according to claim 1, wherein the powder is obtained from the crude product which is solid at 20° C. and unpurified, by using at least one of the techniques selected from the group consisting of:

precipitation in a solvent, cryogenic grinding, and concurrent or countercurrent spray-drying in a cold stream.

15. A composition according to claim 1, wherein the said supplementary additive is selected from the group consisting of:

(a) an aluminum or magnesium sulfate;

(b) a hydrotalcite;

(c) an organic alcohol;

(d) an organic polyol;

(e) a salt or a metal chosen from calcium, barium, magnesium and strontium;

(f) an organic zinc compound;

(g) a lead compound;

(h) an organic phosphate;

(i) a polyorganosiloxane oil; and (j) an epoxide compound; and mixtures thereof.

* * * * *